United States Patent [19]
Driscoll et al.

[11] Patent Number: 6,074,560
[45] Date of Patent: Jun. 13, 2000

[54] USE OF AN IN-LINE FILTER IN THE PREPARATION OF TOTAL NUTRIENT ADMIXTURES

[75] Inventors: David F. Driscoll, West Bridgewater; Bruce R. Bistrian, Ipswich, both of Mass.

[73] Assignee: Beth Israel Deaconess Medical Center, Inc., Boston, Mass.

[21] Appl. No.: 08/781,008

[22] Filed: Jan. 9, 1997

Related U.S. Application Data

[60] Provisional application No. 60/009,904, Jan. 11, 1996.

[51] Int. Cl.⁷ ............................. B01D 39/00; B01D 61/00
[52] U.S. Cl. ............................................ 210/650; 210/651
[58] Field of Search ..................................... 210/650, 651, 210/767, 435; 604/4; 422/101, 102

[56] References Cited

U.S. PATENT DOCUMENTS

| | | | |
|---|---|---|---|
| 5,252,222 | 10/1993 | Matkovich et al. | 210/650 |
| 5,536,413 | 7/1996 | Bormann et al. | 210/650 |

FOREIGN PATENT DOCUMENTS wo 932202   11/1993   WIPO .

OTHER PUBLICATIONS

Puntis, J. et al., "Hazards of parenteral treatment: do particles count?", Arch. Dis. Child., vol. 67, pp. 1475–1477 (1992) .

Driscoll, D.F. et al. "Physiochemical Stability of Total Nutrient Mixtures",*Am J Health–Syst Pharm*, 52:623–633 (1995).

*Primary Examiner*—John Kim
*Attorney, Agent, or Firm*—Lahive & Cockfield, LLP

[57] ABSTRACT

A method for reducing the number lipid droplets having a diameter exceeding a preselected threshold in a nutritional emulsion has been developed. The method has the steps of passing the nutritional emulsion, under pressure, through a filter having a pore size smaller than the threshold. A filter having a mean pore size of about 1.2 $\mu$m with a standard deviation of about 0.5 is sufficient to exclude lipid droplets having a diameter in excess of five $\mu$m.

10 Claims, No Drawings

USE OF AN IN-LINE FILTER IN THE PREPARATION OF TOTAL NUTRIENT ADMIXTURES

This application claims the benefit under 35 U.S.C. 119(e) of U.S. Provisional Application No. 60/009,904 filed Jan. 11, 1996.

BACKGROUND OF THE INVENTION

A recent FDA Safety Alert recommends in-line filtration for all TPN admixtures. Although rigid crystalline particulates can be effectively removed by in-line filters, the fate of flexible lipid droplets enlarged through electromechanical destabilization is less clear. Lipid droplets having diameters greater than 5 microns ($\mu$m) could lodge in the pulmonary microvasculature and produce an embolic syndrome. Recent evidence suggests that total nutritional admixtures (TNAs) in which lipid droplets having a diameter in excess of 5 $\mu$m or more constitute more than 0.4% of the final fat concentration are unstable.

On Apr. 18, 1994 the Food and Drug Administration (FDA) issued a nationwide Safety Alert reporting two deaths and at least two cases of respiratory distress that appear to have resulted from calcium phosphate precipitants present in extemporaneously prepared, lipid emulsion-containing TNAs intended for intravenous administration. To avoid similar tragedies, the FDA has requested commercial suppliers of parenteral nutrients to develop data that might eventually be used to revise relevant labeling instructions involving parenteral nutrient (PN) infusions containing calcium and phosphate salts. In addition, seven specific recommendations were made by the FDA in order to avoid the dangers associated with calcium phosphate precipitation. In particular, the FDA recommended the use of "air-eliminating filters" for all PN admixtures. Specifically, 1.2 $\mu$m porosity membrane in-line filters were suggested for fat emulsion-containing PN dispersions and 0.22 $\mu$m in-line filters for fat emulsion-free PN solutions. Although rigid crystalline particulates, such as dibasic calcium phosphate (CaHPO$_4$), can be effectively removed by in-line filters, the fate of flexible lipid droplets enlarged through electromechanical destabilization is less clear. The degree of destabilization of TNAs is related to the composition of the formulation that often varies in accordance with the patient's clinical condition.

The malleable characteristics or deformability of lipid droplets, coupled with a pressurized pump infusion, may allow the passage of droplets having diameters in excess of 1.2 microns through in-line filters having a pore size of 1.2 microns in much the same way that the deformability of red blood cells allows them to pass through blood vessels, such as capillaries, that are a fraction of their size. Although abnormally large lipid droplets may maneuver through the pulmonary microvasculature, it is equally possible that the administration of sufficiently large numbers of lipid droplets having diameters greater than 5 $\mu$m could produce an embolic syndrome (i.e., the equivalent of a toxic pharmacological dose). Although the precise toxic dose of enlarged fat globules from unstable TNAs is not known, if droplets having a diameter in excess of 5 microns constitute more than 0.4% of the final fat concentration, the resulting mixture is unstable and unfit for administration.

A typical parenteral infusion pump routinely used to deliver PN therapy provides infusion under pressure at values up to 10–15 pounds per square inch (PSI). Since 1 PSI is approximately equal to 50 mm Hg, these infusion pressures are 25 to 50 times higher than the usual mean pulmonary artery pressures. Such ex vivo conditions may enhance the passage of pliable, yet clinically dangerous, lipid droplets. Therefore, the study conditions presented here pose a considerable stress in the in-line filter, in terms of production of excessively large lipid droplets which might not traverse the pulmonary circulation.

Although the problem of microvascular clogging or embolic syndrome is not as prevalent for other types of emulsions for patient use, emulsions having large lipid droplets reflect an unstable admixture and may cause additional health problems. Accordingly, while the use of in-line filters described herein is most advantageous for lipid-containing parenteral nutrition admixtures, it can be used for other nutritional admixtures or other lipid containing emulsions.

An object of the invention is to provide a method for reliably reducing the number of dangerously large lipid droplets from a TNA mixture prior to intravenous administration.

A further object of the invention is to provide a method of parenteral feeding while reducing the number of large lipid droplets in the parenteral feeding admixture.

Another object of the invention is to provide a reduction in large lipid droplets in emulsions.

These and other objects and features of the invention will be apparent from the summary of the invention and the claims.

SUMMARY OF THE INVENTION

The present invention features a method of removing large lipid droplets or globules from lipid containing emulsions destined for patient use can be accomplished using in-line filters. More particularly, it has been found that use of filters having pore sizes smaller than the lipid droplets which are sought to be removed will remove a substantial portion of the lipid droplets while providing sufficient flow properties. In a preferred embodiment, a Total Nutrient Admixture Filter having a pore size of 1.2 microns, such as that available from Pall Biomedical Products Company of East Hills, N.Y., under the designation of TNA1™, when used as an in-line filter for TNA, is effective to trap flexible lipid droplets having diameters in excess of 5 $\mu$m. This is somewhat surprising in that the flexible droplets can deform and pass through the filter despite the difference in pore size versus droplet diameter.

The method for reducing the number of lipid droplets having a diameter larger than a selected threshold in a nutritional admixture has the steps of providing a filter having a pore size smaller than the threshold and passing the nutritional admixture to be filtered through the filter under pressure. Preferably, a pressure of 8–20 PSI is used, with 10–15 PSI being most preferred. This type of pressure can be provided by infusion pumps or other devices known in the art. The threshold is selected so that the emulsion is stable and that if the nutrition admixture is used parenterally, the threshold is selected such that droplets larger than the threshold have the tendency to block microvessels and have the potential to cause embolisms. The normal threshold is about 5 $\mu$m and the preferred pore size is 1–2 $\mu$m. Most preferred filters have a pore size of about 1.2 $\mu$m with a standard deviation of 0.5 $\mu$m.

Another embodiment of the invention provides a method for infusing lipid-containing parenteral nutrition admixtures to patients in a manner to prevent large lipid droplets from entering the patient. This method has the steps of filtering the admixture before introduction into the patient, the filtering being accomplished by utilizing an infusion pump to force the admixture through a filter which has a pore size smaller than the lipid droplets sought to be eliminated while maintaining sufficient flow into said patient. The same pore filters and infusion pumps as previously described can be used.

The effectiveness of a commercially available 1.2 μm in-line filter in preventing the passage of abnormally large and potentially dangerous fat globules is described in the following detailed description.

DETAILED DESCRIPTION OF THE INVENTION

The present invention provides a method infusing a patient with a nutritional emulsion or admixture while reducing the number of large fat or lipid droplets in the nutritional emulsion. The infusion is carried out in a manner which still provides sufficient flow that the patient while lowering the possibility of embolisms or other adverse effects from fat globules being trapped in the capillaries or other small blood vessels. The method uses an in-line filter with a pore size that is smaller than the diameter of the fat globules to be reduced; e.g., a 1.2 μm filter is used to reduce lipid droplets in the 5 μm diameter range. The fact that this works, however, is surprising since the lipid droplets are deformable and should be able to traverse the filter in an elongated rather than spherical shape, particularly as the admixture is forced through the filter under pressure.

The following example will illustrate the efficacy of the invention.

EXAMPLE

In this Example, a reduction in lipid droplets above the preselected cut-off point, 5 μm, was shown using a 1.2 μm filter. The infusion was shown workable for over 24 hours with acceptable flow rate and post filter lipid content, so there cannot be a mere clogging of the filter.

METHODS

Preparation of TNAs

Six pairs of TNAs were aseptically prepared from hospital supplies as 1.5 L formulations in ethylene vinyl acetate infusion bags using an automated compounding device under sterile conditions in a Class 100 laminar airflow hood. All extemporaneously prepared admixtures using the automated compounding device were within 5% of the expected volume. Admixtures that exceeded a 5% compounding error (based on final weight) were deemed unacceptable for study, and the admixtures remade if necessary. All TNA formulations were immediately transferred to the laboratory for time 0 analyses and then placed in a temperature-controlled chamber set at 25° C.±0.1° C.

Four clinically relevant 1.5 L TNA dispersions of varying degrees of stability were prepared in duplicate and studied over 30 hours. Each of these eight formulations studied represented a single, concentrated macronutrient formula having standard concentrations of electrolytes and micronutrients. However, to induce electromechanical stress, the concentration of divalent cations (as magnesium and calcium) was progressively increased in these eight formulations from one to three times the usual dosage corresponding to the parenteral equivalent of the oral recommended dietary allowances (RDAs) for these electrolytes. In addition, an admixture that had previously exhibited unstable characteristics was made in duplicate on two separate occasions and similarly analyzed in order to ensure adequate physiochemical stress to the TNA, and thus, sufficiently challenge the in-line filter studied. This admixture was described in Driscoll D. F., Bhargava H. N., Li L. et al. Physicochemical stability of total nutrient admixtures. Am J. Health-Syst Pharm. 52:623–34, 1995.

A total of 12 admixtures were studied and their compositions appear in Table 1. Admixture composition was varied primarily for its effects on lipid droplet stability since the measurement of the efficiency of the in-line filter was the principle goal in this study.

TABLE 1

PROFILES OF TNA FORMULAS STUDIED

| | FORMULA No. | | | | |
|---|---|---|---|---|---|
| | I | II | III | IV | V |
| Amino Acids[i] (g) | 90 | 90 | 90 | 90 | 51 |
| Dextrose[j] (g) | 270 | 270 | 270 | 270 | 120 |
| Lipids[k] (g) | 30 | 30 | 30 | 30 | 36 |
| Sodium[l] (mEq) | 100 | 100 | 100 | 100 | 23 |
| Potassium[m] (mEq) | 80 | 80 | 80 | 80 | 23 |
| Calcium[n] (mEq) | 9.4 | 14.1 | 18.8 | 28.2 | 12.6 |
| Magnesium[o] (mEq) | 8.1 | 12.2 | 16.2 | 24.2 | 12.6 |
| Phosphorus (mmol) | 30 | 30 | 30 | 30 | 22.5 |
| Chloride (mEq) | 140 | 140 | 140 | 140 | 14 |
| Trace Elements[p] (mL) | 3 | 3 | 3 | 3 | 3 |
| Multivitamins[q] (mL) | 10 | 10 | 10 | 10 | 10 |
| Heparin[r] (units) | 3000 | 3000 | 3000 | 3000 | 3000 |
| Total TNA Volume(mL) | 1500 | 1500 | 1500 | 1500 | 1500 |
| Flow Rate (ML · hr$^{-1}$) | 55 | 55 | 55 | 55 | 55 |

Sampling of TNAs

Quantification of abnormal lipid droplets was determined from triplicate particle counts taken 0, 6, 24 and 30 hours after preparation. At six hours, a simulated patient infusion was begun using a diethylhexylphthalate (DEHP)-free administration set attached to a corresponding administration infusion pump set at a continuous flow rate of 55 ml/hour through a TNA1™ 1.2 μm in-line filter. The pump operated up to a maximum pressure of 10 PSI. Operation of the pump at pressures in excess of 10 PSI resulted in an occlusion alarm stopping the pump. Pre- and post-filtration samples were taken at 6, 24 and 30 hours. These correspond to 0, 18 and 24 hours of simulated patient infusion.

TNA Analysis

All lipid droplets were presumed to be spherical a shape that represents the minimum surface area for a given geometric volume. In fact, micrometric determination of asymmetric solid particles, such as crystalline precipitants, frequently relies on equivalent spherical diameters. Unlike lipid droplets, whose actual shape tends to be spherical, asymmetric rigid crystalline particles are generally far from spherical. As a result, the use of equivalent diameters to estimate the concentration of abnormal lipid droplets present in an unstable TNA formulation is more precise, than similar determinations of rigid, less spherical crystalline matter. Laser light extinction enables the quantification of specific amounts of abnormal lipid droplets that would greatly assist studies of TNA stability and subsequent toxicity. Thus, laser light extinction was viewed as the most appropriate and sensitive measure of TNA stability in this study.

Particle counts were determined at each time interval using a single particle optical sensing device, HRLD-150 laser diode sensor with model 3000A syringe-operated sampler, HIAC/Royco, Silver Spring, Md. and Accusizer 770 Software Program, Nicomp Particle Sizing Systems, Santa Barbara, Calif., that employs laser light extinction to detect enlarge fat globules resulting from destabilization of the TNA formulation. The above method is well-known in the prior art.

Data Analysis

Two independent factors were studied:

(1.) changes in the concentration of enlarged lipid droplets with time, and (2.) the difference between the concentration of abnormally enlarged lipid droplets from TNA dispersions of varying physicochemical stability just prior to filtration through a TNA1™ 1.2 μm in-line filter and the concentration of abnormally enlarged lipid droplets immediately after filtration.

The presence of enlarged lipid droplets that characterized the performance of the in-line filter in this study was determined by individually number-weighting the quantity of lipid droplets having diameters greater than 1.75 μm, (instrument threshold for detecting abnormal fat globules expressed as LD2) and the quantity of lipid droplets having diameters greater than 5 μm (theoretical physiologic threshold for embolic syndrome expressed as LD1), and as the LD1/LD2 ratio.

The concentration of enlarged fat globules that may pose a clinical risk, as well as characterize the stability of the TNAs studied, was determined by volume-weighting the total percent fat present in droplets having a diameter greater than 5 μm (PFAT), and applying the following general equation:

$$PFAT = \frac{\left( \begin{array}{l} TSV\ (cm^3) \times \text{Density of Soybean Oil} \\ (g/cm^2) \times \text{Sample Dilution Factor } (cm^3) \times 100 \end{array} \right)}{(\text{Sample Volume } (cm^3) \times \text{Final Fat Composition of } TNA\ (g/cm^3))}$$

where: TSV=total spherical volume of all lipid droplets having diameters in excess of 5 μm.

Thus, a total of four dependent variable analyses were compared to treatment and time. These were: three number-weighted variables (LD1, LD2 and the LD1/LD2 ratio), and one volume-weighted variable (PFAT).

All data is expressed as mean ±SD. Statistical analyses of the quantified lipid droplets, accomplished by laser light extinction was performed by a two-way repeated measurement of analysis of variance (ANOVA) assessing treatment (pre- vs. post filtration) and time (changes in droplet size over 30 hours). The a priori level of significance was set at 0.05. A Systat™ Program, version 2.2, was used to perform statistical evaluations.

RESULTS

The data and its statistical analysis is summarized in Table 2. Significant differences for treatment and time were found for each variable analyzed (Table 3). In all cases, time was, as expected, a significant factor as the stability of all extemporaneously prepared admixtures deteriorates with time. Of the number-weighted variables, significant post-filtrate reductions in the number of lipid droplets having diameters in excess of 5 microns (LD1), (p=0.041) and those having diameters in excess of 1.75 microns (LD2), (p<0.001) were noted.

TABLE 2

SUMMARY OF DATA FOR TNA FORMULATIONS STUDIED

| | PRE-FILTER | | | | POST-FILTER | | | |
|---|---|---|---|---|---|---|---|---|
| | LD1 | LD2 | LD1/LD2* | PFAT | LD1 | LD2 | LD1/LD2 | PFAT |
| TNA 1A | | | | | | | | |
| 0 hr. | 35 ± 7 | 939 ± 4122 | 3.7 ± 0.8 | 0.009 ± 0.008 | — | — | — | — |
| 6 hr. | 40 ± 1 | 1302 ± 19 | 3.1 ± 0.1 | 0.012 ± 0.004 | 19 ± 5 | 121 ± 4 | 15.6 ± 2.8 | 0.004 ± 0.003 |
| 24 hr. | 21 ± 5 | 9561 ± 7 | 2.2 ± 0.5 | 0.004 ± 0.002 | 17 ± 5 | 309 ± 11 | 5.5 ± 1.8 | 0.002 ± 0.001 |
| 30 hr | 17 ± 5 | 1265 ± 13 | 1.4 ± 0.4 | 0.003 ± 0.003 | 24 ± 3 | 2711 ± 6 | 9.0 ± 1.5 | 0.003 ± 0.001 |
| TNA IB | | | | | | | | |
| 0 hr. | 39 ± 4 | 1121 ± 28 | 3.5 ± 0.3 | 0.018 ± 0.016 | — | — | — | — |
| 6 hr. | 32 ± 3 | 1298 ± 33 | 2.4 ± 0.2 | 0.006 ± 0.003 | 22 ± 3 | 242 ± 7 | 9.2 ± 1.4 | 0.003 ± 0.002 |
| 24 hr. | 21 ± 7 | 1251 ± 49 | 1.7 ± 0.6 | 0.003 ± 0.001 | 15 ± 1 | 240 ± 4 | 6.3 ± 0.5 | 0.002 ± 0.001 |
| 30 hr | 76 ± 6 | 3180 ± 26 | 2.4 ± 0.2 | 0.012 ± 0.001 | 19 ± 3 | 204 ± 5 | 9.3 ± 1.5 | 0.003 ± 0.001 |
| TNA 2A | | | | | | | | |
| 0 hr. | 29 ± 6 | 806 ± 28 | 3.7 ± 0.8 | 0.005 ± 0.002 | — | — | — | — |
| 6 hr. | 18 ± 4 | 983 ± 39 | 2.1 ± 0.3 | 0.003 ± 0.001 | 26 ± 13 | 252 ± 15 | 10.2 ± 4.5 | 0.006 ± 0.004 |
| 24 hr. | 15 ± 2 | 969 ± 22 | 1.6 ± 0.2 | 0.002 ± 0.001 | 59 ± 6 | 404 ± 6 | 14.7 ± 1.3 | 0.020 ± 0.003 |
| 30 hr | 19 ± 5 | 984 ± 53 | 2.0 ± 0.4 | 0.003 ± 0.002 | 88 ± 8 | 417 ± 15 | 21.1 ± 2.8 | 0.031 ± 0.003 |
| TNA 2B | | | | | | | | |
| 0 hr. | 28 ± 10 | 876 ± 31 | 3.2 ± 1.3 | 0.005 ± 0.002 | — | — | — | — |
| 6 hr. | 18 ± 4 | 899 ± 37 | 2.0 ± 0.5 | 0.003 ± 0.001 | 24 ± 4 | 298 ± 9 | 8.1 ± 1.2 | 0.004 ± 0.001 |
| 24 hr. | 17 ± 2 | 793 ± 24 | 2.2 ± 0.2 | 0.003 ± 0.001 | 30 ± 7 | 326 ± 23 | 9.2 ± 1.7 | 0.005 ± 0.003 |
| 30 hr | 15 ± 7 | 847 ± 51 | 1.8 ± 0.7 | 0.002 ± 0.002 | 62 ± 3 | 273 ± 13 | 22.6 ± 0.4 | 0.024 ± 0.005 |
| TNA 3A | | | | | | | | |
| 0 hr. | 45 ± 5 | 1065 ± 29 | 4.2 ± 0.4 | 0.009 ± 0.002 | — | — | — | — |
| 6 hr. | 18 ± 4 | 899 ± 37 | 2.0 ± 0.5 | 0.003 ± 0.001 | 24 ± 4 | 298 ± 9 | 8.1 ± 1.2 | 0.004 ± 0.001 |
| 24 hr. | 17 ± 2 | 793 ± 24 | 2.2 ± 0.2 | 0.003 ± 0.001 | 30 ± 7 | 326 ± 23 | 9.2 ± 1.7 | 0.005 ± 0.003 |

TABLE 2-continued

SUMMARY OF DATA FOR TNA FORMULATIONS STUDIED

| | PRE-FILTER | | | | POST-FILTER | | | |
|---|---|---|---|---|---|---|---|---|
| | LD1 | LD2 | LD1/LD2* | PFAT | LD1 | LD2 | LD1/LD2 | PFAT |
| 30 hr | 15 ± 7 | 847 ± 51 | 1.8 ± 0.7 | 0.002 ± 0.002 | 62 ± 3 | 273 ± 13 | 22.6 ± 0.4 | 0.024 ± 0.005 |
| | | | | TNA 3B | | | | |
| 0 hr. | 44 ± 5 | 1103 ± 56 | 4.0 ± 0.4 | 0.007 ± 0.001 | — | — | — | — |
| 6 hr. | 41 ± 10 | 1221 ± 24 | 3.3 ± 0.8 | 0.006 ± 0.003 | 15 ± 3 | 151 ± 6 | 9.8 ± 2.3 | 0.002 ± 0.002 |
| 24 hr. | 24 ± 2 | 1187 ± 36 | 2.0 ± 0.1 | 0.003 ± 0.001 | 14 ± 4 | 148 ± 19 | 9.7 ± 2.4 | 0.002 ± 0.002 |
| 30 hr | 21 ± 4 | 1318 ± 28 | 1.6 ± 0.3 | 0.003 ± 0.001 | 53 ± 4 | 324 ± 15 | 16.3 ± 2.0 | 0.18 ± 0.006 |
| | | | | TNA 4A | | | | |
| 0 hr. | 58 ± 9 | 1214 ± 45 | 4.8 ± 0.6 | 0.011 ± 0.005 | — | — | — | — |
| 6 hr. | 34 ± 5 | 1298 ± 17 | 2.6 ± 0.4 | 0.003 ± 0.001 | 24 ± 4 | 298 ± 9 | 8.1 ± 1.2 | 0.004 ± 0.001 |
| 24 hr. | 31 ± 3 | 1140 ± 20 | 2.7 ± 0.2 | 0.004 ± 0.001 | 44 ± 8 | 434 ± 16 | 10.0 ± 1.6 | 0.010 ± 0.005 |
| 30 hr | 22 ± 8 | 1250 ± 7 | 1.7 ± 0.6 | 0.003 ± 0.001 | 15 ± 4 | 153 ± 11 | 9.7 ± 1.7 | 0.004 ± 0.002 |
| | | | | TNA 4B | | | | |
| 0 hr. | 71 ± 6 | 1485 ± 18 | 4.8 ± 0.4 | 0.011 ± 0.004 | — | — | — | — |
| 6 hr. | 65 ± 6 | 1933 ± 26 | 3.4 ± 0.2 | 0.011 ± 0.002 | 14 ± 1 | 131 ± 14 | 10.8 ± 1.4 | 0.003 ± 0.002 |
| 24 hr. | 45 ± 5 | 1557 ± 12 | 2.9 ± 0.3 | 0.008 ± 0.003 | 60 ± 3 | 514 ± 25 | 11.6 ± 0.8 | 0.014 ± 0.001 |
| 30 hr | 56 ± 2 | 2232 ± 68 | 2.5 ± 0.2 | 0.009 ± 0.001 | 23 ± 3 | 238 ± 18 | 9.9 ± 2.0 | 0.004 ± 0.000 |
| | | | | TNA 5A | | | | |
| 0 hr. | 176 ± 5 | 2805 ± 19 | 6.3 ± 0.1 | 0.031 ± 0.004 | — | — | — | — |
| 6 hr. | 103 ± 9 | 2642 ± 20 | 3.9 ± 0.3 | 0.012 ± 0.003 | 51 ± 12 | 527 ± 40 | 9.8 ± 3.0 | 0.010 ± 0.003 |
| 24 hr. | 225 ± 8 | 3190 ± 2 | 7.0 ± 0.3 | 0.035 ± 0.002 | 65 ± 9 | 545 ± 33 | 11.9 ± 1.5 | 0.012 ± 0.005 |
| 30 hr | 306 ± 32 | 3778 ± 48 | 8.1 ± 0.7 | 0.061 ± 0.004 | 190 ± 8 | 581 ± 15 | 32.8 ± 2.0 | 0.055 ± 0.006 |
| | | | | TNA 5B | | | | |
| 0 hr. | 160 ± 16 | 2648 ± 26 | 6.0 ± 0.6 | 0.032 ± 0.005 | — | — | — | — |
| 6 hr. | 114 ± 3 | 2585 ± 33 | 4.4 ± 0.1 | 0.017 ± 0.001 | 15 ± 2 | 199 ± 27 | 7.6 ± 1.3 | 0.001 ± 0.000 |
| 24 hr. | 279 ± 20 | 2458 ± 124 | 11.3 ± 0.3 | 0.052 ± 0.004 | 39 ± 1 | 482 ± 18 | 8.0 ± 0.6 | 0.006 ± 0.002 |
| 30 hr | 553 ± 15 | 4001 ± 19 | 13.8 ± 0.3 | 0.104 ± 0.006 | 189 ± 19 | 816 ± 22 | 23.2 ± 1.7 | 0.055 ± 0.011 |
| | | | | TNA 5C | | | | |
| 0 hr. | 99 ± 7 | 2359 ± 76 | 4.2 ± 0.2 | 0.015 ± 0.005 | — | — | — | — |
| 6 hr. | 78 ± 12 | 2457 ± 84 | 3.2 ± 0.4 | 0.009 ± 0.002 | 32 ± 7 | 444 ± 24 | 7.4 ± 1.9 | 0.006 ± 0.003 |
| 24 hr. | 1272 ± 17 | 3998 ± 38 | 31.8 ± 0.7 | 0.574 ± 0.004 | 109 ± 2 | 1143 ± 53 | 9.6 ± 0.5 | 0.030 ± 0.008 |
| 30 hr | 1785 ± 12 | 6225 ± 49 | 28.7 ± 0.4 | 0.823 ± 0.027 | 1882 ± 2 | 7773 ± 33 | 24.3 ± 0.3 | 0.484 ± 0.059 |
| | | | | TNA 5D | | | | |
| 0 hr. | 33 ± 4 | 1050 ± 47 | 3.1 ± 0.3 | 0.004 ± 0.001 | — | — | — | — |
| 6 hr. | 56 ± 9 | 1553 ± 41 | 3.8 ± 0.8 | 0.006 ± 0.001 | 50 ± 11 | 833 ± 12 | 5.9 ± 1.2 | 0.078 ± 0.005 |
| 24 hr. | 3007 ± 73 | 7245 ± 116 | 41.5 ± 0.4 | 1.028 ± 0.054 | 1359 ± 5 | 6685 ± 52 | 20.6 ± 0.1 | 0.454 ± 0.052 |
| 30 hr | 5530 ± 110 | 9980 ± 109 | 55.4 ± 0.5 | 2.648 ± 0.001 | 1435 ± 16 | 15817 ± 195 | 9.1 ± 2.0 | 0.477 ± 0.020 |

TABLE 3

RESULTS OF DEPENDENT VARIABLE ANALYSES

| TREATMENT INTERACTION | | TIME | |
|---|---|---|---|
| VARIABLE | PRE-FILTER | POST-FILTER | HOURS |
| TREATMENT TIME | | | |
| LD > 5 $\mu m^a$ | 53 ± 31 | 25 ± 14 | 0 |
| (LD1) | 414 ± 865 | 152 ± 370 | 18 |
| | 702 ± 1556 | 336 ± 611 | 24 |
| SIGNIFICANCE | p = 0.041 | p < 0.001 | p = 0.416 |
| LD ≧ 1.75 $\mu m^a$ | 1637 ± 599 | 294 ± 206 | 0 |
| (LD2) | 2146 ± 1843 | 941 ± 1744 | 18 |
| | 3014 ± 2660 | 2258 ± 4638 | 24 |
| SIGNIFICANCE | p < 0.001 | p < 0.0001 | p = 0.750 |
| LD1/LD2 ratio[a] | 3.1 ± 0.8 | 9.5 ± 2.9 | 0 |
| (as 10%) | 9.0 ± 13.0 | 10.3 ± 4.2 | 18 |
| | 10.2 ± 15.9 | 17.1 ± 7.7 | 24 |
| SIGNIFICANCE | p < 0.001 | p < 0.0001 | p = 0.126 |
| PFAT > 5 $\mu m^b$ | 0.008 ± 0.005 | 0.004 ± 0.003 | 0 |
| | 0.143 ± 0.314 | 0.046 ± 0.126 | 18 |
| SIGNIFICANCE | p = 0.029 | p = 0.003 | p = 0.203 |

[a]Number-weighted variable
[b]Volume-weighted variable

Analysis of the LD1/LD2 ratio demonstrated a significantly higher percentage of enlarged droplets in the post-filtrate sample (p<0.001). In addition, a post hoc analysis of the fractional reductions between the pre- and post-filtration concentrations for LD1 and LD2 populations was performed. Of the 108 pre- to post-filtration analyses examined during the simulated 24 hour infusion, fractional reductions were observed in 71/108 (66%) LD1 cases and in 102/108 (94%) LD2 cases, demonstrating a greater reduction for the smaller vs. the larger droplets by $\chi^2$ analysis (p<0.000001). Both of these number-weighted observations in the post-filtrate sample may reflect the effects of filtration on electrically destabilized lipid droplets.

Of greatest importance, when the potentially dangerous lipid droplets having diameters in excess of 5 microns were appropriately quantified, and thus weighted by volume, it was discovered that their numbers were also significantly reduced by the in-line filter (p=0.029). Hence, total exposure to large and potentially clinically meaningful unstable lipid droplets was significantly reduced by the TNA1™ in-line filter. No significant interaction effects were noted between treatment and time.

DISCUSSION OF RESULTS

Total nutrient admixtures are stabilized by a naturally occurring emulsifier that is a mixture of egg yolk phosphatides. Physicochemical stability is determined by the ability of the emulsifier to resist abnormal changes in the size and number of enlarged lipid droplets, thus maintaining a homogenous dispersion of fine lipid droplets having diameters in the range of 0.25–0.5 $\mu$m. The emulsifier accomplishes emulsion stability through the formation of a molecular film around each submicron lipid droplet. This film acts as a barricade, cushioning the blow from surrounding lipid droplets that stray into its collision path. The emulsion film is a closely packed arrangement of hydrophobic tails embedded within the oil phase or droplet, as well as hydrophilic heads that simultaneously project into the aqueous phase. The result is a rigid liquid crystalline film that produces an effective barrier to coalescence.

At typical pH profiles encountered in PN admixtures, the polar phosphate groups at a hydrophilic heads are ionized, producing a net negative charge at the surface of each fat globule. This results in an electrostatic barrier between lipid droplets.

Together, the molecular film on a droplet and the electrostatic repulsion between droplets produce a homogenous and electromechanically stable lipid emulsion.

During the formulation of a TNA prescription, large quantities of cations may be introduced to treat severe metabolic disturbances. These useful clinical maneuvers may, however, disrupt the dispersion. The higher the cation valence, the greater the destabilization potential in the final TNA product. A diminution in the electrostatic charge as a result of extreme cationic insult weakens the stabilizing forces associated with electrostatic repulsion. This results in adverse changes in the physicochemical characteristics of the finely dispersed lipid droplets, decreasing the safe distance between droplets and thereby increasing the probability of particle collisions. As the surface charge approaches neutrality, the frequency of lipid droplet collisions increases dramatically. With each collision, the integrity of the rigid monomolecular film surrounding each droplet is compromised and the risk of forming enlarged fat globules increases. This enhances TNA emulsion destabilization and increases the danger of the infusion. Each concentrated macronutrient formula common to TNA formulations I–IV was stable throughout the study (i.e., PFAT<0.4%) even though calcium and magnesium concentrations were increased up to three times the parenteral equivalent of the recommended dietary allowance (RDA). This finding supports the protective role of high final concentrations of amino acids and dextrose in ensuring TNA stability. By contrast, formulation V clearly demonstrates the devastating impact of iron dextran in combination with low amino acid and dextrose final concentrations on admixture stability.

In this study, the TNA1™ filter reduced the number of electromechanically destabilized lipid droplets having diameter greater than 5 $\mu$m (LD1) and lipid droplets having diameters greater than 1.75 $\mu$m (LD2), as well as the quantitatively more important, volume-weighted percent of lipid droplets having diameters greater than 5 $\mu$m (PFAT). However, although this finding may not be clinically important, the ratio of large droplets to total droplets (LD1/LD2) was significantly increased in the post-filtrate samples.

These lipid droplets undergo important physicochemical changes that impair the stability and the subsequent behavior of emulsion droplets. As the lipid droplets coalesce to form larger droplets the mechanical film around the surface of each lipid droplet readjusts to accommodate the change in dimension. Presumably, this action continually reduces the rigidity and alters the surface energy of the mechanical film with each expansion in the droplet's size. The newly formed droplet becomes less stable due to this disruption in film integrity and it loses the stabilizing viscoelastic behavior of an otherwise stable liquid crystalline film. This increase in film flexibility may explain the higher LD1/LD2 ratio. A flexible film would permit lipid droplets to deform more readily. This increased deformability would permit a lipid droplet to pass through a filter pore much smaller than the diameter of the lipid droplet. The combination of reduced film integrity coupled with a pressurized infusion may augment the passage of these abnormal lipid droplets.

Conversely, the smaller lipid droplets are more easily trapped by a more stable, rigid film. The post hoc analysis of the differences in the fractional reduction between LD1 and LD2 populations lends further support to this contention. Although this finding was unexpected, it appears to be principally of academic interest, as the clinically important volume-weighted concentration of enlarged lipid droplets, PFAT, as well as the concentration of droplets of all sizes were significantly reduced in passing through the filter.

Considering the greater deformability of enlarged lipid droplets, it is surprising that more of these unstable droplets did not pass through the TNA1™ 1.2 $\mu$m filter. Table 2 clearly shows that numerous enlarged lipid droplets did pass through the filter. The passage of these lipid droplets through the filter was presumably facilitated by the deformability associated with lipid droplet instability combined with a normal infusion pressure which tended to push the deformable lipid droplets through the filter.

As lipid droplet size increases through the coalescence, the rigidity of the monomolecular film diminishes, producing a more flexible film that allows deformation of lipid droplets at infusion pressures near 10 PSI. This facilitates the passage of lipid droplets through a pore size a fraction of their diameter. Despite this, the TNA1™ filter retained the majority of these lipid droplets, as is evident from the volume-weighted data shown in Table 2 comparing pre- and post-filtrate samples. Despite the infusion of highly unstable TNA formulations having PFAT concentrations as high as 2.75%, not once during the twenty-four hour infusion period did the filter occlude.

It is possible that the TNA1™ filter may have occluded had the simulated infusion period been extended beyond 24 hours. The data in Table 3 showing the drop in magnitude between the pre and post filtrate concentrations of the LD2 (>1.75 $\mu$m) suggests this possibility. Conceivably the unstable fat globules could eventually fill the 1.2 $\mu$m pores of the TNA1™ filter, thereby occluding the filter.

Although in a few cases the post-filtrate, volume-weighted concentration of abnormally enlarged lipid droplets (PFAT) exceeded the level of pharmaceutical acceptance of 0.4%, the mixture used was a highly stressed formulation used for experimental purposes only and never for clinical purposes.

CONCLUSION

The reported study demonstrated the efficacy of the TNA1™ filter in trapping flexible lipid droplets that exceed the pore size. Even then, the elimination of droplets greater than the pore size is only relative, presumably because the infusion pump in this study operates at supraphysiologic pressures which facilitated the passage of some enlarged fat globules. The results found in this study demonstrate the unique ability of the TNA1™ filter to significantly reduce the number of enlarged lipid droplets. This suggests that in-line filtration and suggesting filtration should be a standard component of TNA therapy.

This example is merely illustrative and not meant to be limiting in any way. Those skilled in the art will determine other modifications to the procedures described herein which are within the scope of the present invention. The present invention is defined by the following claims.

What is claimed is:

1. A method for reducing the number of lipid droplets having a diameter exceeding a preselected threshold in a nutritional emulsion, said method comprising the steps of passing said nutritional emulsion, under pressure, through a filter having a pore size smaller than said threshold.

2. The method as recited in claim 1 wherein said pressure is between 8 and 20 psi across the filter.

3. The method as recited in claim 1 wherein said threshold is selected such that the parenteral introduction of lipid droplets having a diameter in excess of said threshold has the potential to be trapped in the microvessels of a patient and result in an embolism.

4. The method as recited in claim 3 wherein said threshold is substantially 5 $\mu$m and said pore size is between 1 and 2 $\mu$m.

5. The method as recited in claim 1 wherein said filter comprises a total nutritional admixture filter having a mean pore size of about 1.2 $\mu$m with a standard deviation of about 0.5 $\mu$m.

6. A method for infusing a lipid-containing parenteral nutrition admixture to patients in a manner to prevent lipid droplets having a diameter in excess of a preselected threshold in said admixture from entering the patient, said method comprising the steps of preparing said lipid-containing admixture, and infusing said lipid-containing admixture to said patient using an infusion pump through an in-line filter having a preselected pore size smaller than said preselected threshold.

7. The method as recited in claim 6 wherein said infusion pump provides a pressure of between 8 and 20 psi across said filter.

8. The method as recited in claim 6 wherein said large lipid droplets to be removed from said admixture are those that the parenteral introduction of lipid droplets having a diameter exceeding said preselected threshold have the potential to be trapped in the microvessels of a patient and result in an embolism.

9. The method as recited in claim 8 wherein said large droplets are greater than about 5 $\mu$m in diameter and said pore size is between 1 and 2 $\mu$m.

10. The method as recited in claim 6 wherein said filter comprises a total nutritional admixture filter having a mean pore size of about 1.2 $\mu$m with a standard deviation of about 0.5 $\mu$m.

* * * * *